(12) United States Patent
Cigaina

(10) Patent No.: US 8,792,986 B2
(45) Date of Patent: *Jul. 29, 2014

(54) TREATMENT OF THE AUTONOMIC NERVOUS SYSTEM

(75) Inventor: Valerio Cigaina, Villorba (IT)

(73) Assignee: Medtronic, Inc., Minneapolis, MN (US)

( * ) Notice: Subject to any disclaimer, the term of this patent is extended or adjusted under 35 U.S.C. 154(b) by 280 days.

This patent is subject to a terminal disclaimer.

(21) Appl. No.: 12/706,608

(22) Filed: Feb. 16, 2010

(65) Prior Publication Data

US 2010/0211130 A1    Aug. 19, 2010

Related U.S. Application Data

(63) Continuation of application No. 11/175,626, filed on Jul. 6, 2005, now Pat. No. 7,664,551.

(60) Provisional application No. 60/585,885, filed on Jul. 7, 2004.

(51) Int. Cl.
*A61N 1/00* (2006.01)

(52) U.S. Cl.
USPC .......................................................... 607/40

(58) Field of Classification Search
USPC .......................................................... 607/40
See application file for complete search history.

(56) References Cited

U.S. PATENT DOCUMENTS

| | | |
|---|---|---|
| 3,719,183 A | 3/1973 | Schwartz |
| 4,279,886 A | 7/1981 | Allen |
| 5,188,104 A | 2/1993 | Wernicke et al. |
| 5,231,988 A | 8/1993 | Wernicke et al. |
| 5,263,480 A | 11/1993 | Wernicke et al. |
| 5,292,344 A | 3/1994 | Douglas |
| 5,423,872 A | 6/1995 | Cigaina |
| 5,540,730 A | 7/1996 | Terry, Jr. et al. |
| 5,690,691 A | 11/1997 | Chen et al. |
| 5,716,385 A | 2/1998 | Mittal et al. |
| 5,716,392 A | 2/1998 | Bourgeois et al. |
| 5,836,994 A | 11/1998 | Bourgeois |

(Continued)

FOREIGN PATENT DOCUMENTS

| | | |
|---|---|---|
| WO | WO 88/03389 | 5/1988 |
| WO | WO 01/76690 A1 | 10/2001 |

(Continued)

OTHER PUBLICATIONS

Kang, et al., "Pancreatic Exocrine-Endocrine Interrelationship", Gastroenterology Clinics of North America, 1990; 28 (3):551-569.

(Continued)

*Primary Examiner* — George Manuel
(74) *Attorney, Agent, or Firm* — Shumaker & Sieffert, P.A.

(57) ABSTRACT

Systems and methods are provided for modulating the autonomic nervous system by the electrical stimulation of the neuro-muscular system of a patient, and include an implantable electrical system for gastrointestinal stimulation which incorporates a heart rate sensor to indicate the neurovegetative patient condition, to initiate and terminate stimulation at specific locations, and an algorithm to automatically control electrical stimulation frequency, interval, amplitude, or a combination of such parameters for adaptive treatment of obesity, anorexia, other eating disorders, diseases related with the so called "metabolic syndrome" (e.g., impaired glucose tolerance and diabetes type 2, GERD, systemic hypertension, early arterovascular degeneration, early senility, and the like), and disorders related to a pathologic inbalance of the autonomic nervous system.

20 Claims, 1 Drawing Sheet

(56) References Cited

U.S. PATENT DOCUMENTS

| | | | |
|---|---|---|---|
| 5,861,014 A | 1/1999 | Familoni | |
| 5,916,216 A | 6/1999 | DeSatnick et al. | |
| 5,919,216 A | 7/1999 | Houben et al. | |
| 5,928,272 A | 7/1999 | Adkins et al. | |
| 6,083,249 A | 7/2000 | Familoni | |
| 6,097,984 A | 8/2000 | Douglas | |
| 6,185,452 B1 | 2/2001 | Schulman et al. | |
| 6,208,894 B1 | 3/2001 | Schulman et al. | |
| 6,216,039 B1 | 4/2001 | Bourgeois | |
| 6,238,423 B1 | 5/2001 | Bardy | |
| 6,315,721 B2 | 11/2001 | Schulman et al. | |
| 6,327,503 B1 | 12/2001 | Familoni | |
| 6,341,236 B1 | 1/2002 | Osorio et al. | |
| 6,535,764 B2 | 3/2003 | Imran et al. | |
| 6,571,127 B1 | 5/2003 | Ben-Haim et al. | |
| 6,600,953 B2 | 7/2003 | Flesler et al. | |
| 6,735,477 B2 | 5/2004 | Levine | |
| 6,754,536 B2 | 6/2004 | Swoyer et al. | |
| 6,832,114 B1 | 12/2004 | Whitehurst et al. | |
| 6,853,862 B1 | 2/2005 | Marchal et al. | |
| 6,885,888 B2 | 4/2005 | Rezai | |
| 6,895,278 B1 | 5/2005 | Gordon | |
| 6,928,320 B2 | 8/2005 | King | |
| 7,167,750 B2 * | 1/2007 | Knudson et al. | 607/40 |
| 7,236,822 B2 * | 6/2007 | Dobak, III | 607/2 |
| 7,263,405 B2 | 8/2007 | Boveja et al. | |
| 7,374,541 B2 * | 5/2008 | Amitzur et al. | 600/485 |
| 7,664,551 B2 | 2/2010 | Cigaina | |
| 2002/0016344 A1 | 2/2002 | Tracey | |
| 2002/0087192 A1 | 7/2002 | Barrett et al. | |
| 2002/0128563 A1 | 9/2002 | Carlson et al. | |
| 2002/0198470 A1 | 12/2002 | Imran et al. | |
| 2003/0018367 A1 | 1/2003 | DiLorenzo | |
| 2003/0181958 A1 | 9/2003 | Dobak, III | |
| 2003/0181959 A1 | 9/2003 | Dobak, III | |
| 2004/0088022 A1 | 5/2004 | Chen | |
| 2004/0111033 A1 | 6/2004 | Oung et al. | |
| 2004/0172084 A1 | 9/2004 | Knudson et al. | |
| 2004/0193229 A1 | 9/2004 | Starkebaum et al. | |
| 2004/0215180 A1 | 10/2004 | Starkebaum et al. | |
| 2004/0236382 A1 | 11/2004 | Dinsmoor et al. | |
| 2004/0249416 A1 | 12/2004 | Yun et al. | |
| 2005/0096638 A1 | 5/2005 | Starkebaum et al. | |
| 2005/0222638 A1 | 10/2005 | Foley et al. | |
| 2008/0132968 A1 | 6/2008 | Starkebaum | |

FOREIGN PATENT DOCUMENTS

| | | |
|---|---|---|
| WO | WO 02/38217 A2 | 5/2002 |
| WO | WO 02/087657 A2 | 11/2002 |
| WO | WO 02/089655 A2 | 11/2002 |
| WO | WO 03/018113 A1 | 3/2003 |
| WO | WO 2006/010025 A2 | 1/2006 |

OTHER PUBLICATIONS

Holst et al., "Nervous Control of Pancreatic Exocrine Secretion in Pigs", Acta Physiol. Scan, 1979; 105:33-51.

Fiorucci et al., "Duodenal Osmolality Drives Gallbladder Emptying in Humans", Digestive Diseases and Sciences, 1990; 35(6):698-704.

Chen et al., "Serosal and Cutaneous Recordings of Gastric Myoelectrical Activity in Patients with Gastroparesis", American Physiological Society, 1994; 266:G90-G98.

Boissonade et al., "Fos Expression in Ferret Dorsal Vagal Complex After Peripheral Emetic Stimuli", American Physiological Society, 1994; 266(4Pt2):R1118-R1126.

Koch et al., "Electrogastrography", An Illustrated Guide to Gastrointestinal Motility, 1993; 2nd Edition: 290-307.

Koch et al. "Functional Disorders of the Stomach", Seminars in Gastrointestinal Disease, 1996; 7(4):185-195.

Koch, "Gastroparesis: Diagnosis and Management", Practical Gastroenterology, GI Motility Series #8, 1997; 30-43.

Familoni et al., "Efficacy of Electrical Stimulation at Frequencies Higher than Basal Rate in Canine Stomach", Digestive Diseases and Sciences, 1997; 42(5):892-897.

Grundy et al., "Effects of Stimulation of the Vagus Nerve in Bursts on Gastric Acid Secretion and Motility in the Anaesthetized Ferret", J. Physiol., 1982; 333:451-461.

Sjodin, "Gastric Acid Responses to Graded Vagal Stimulation in the Anaesthetized Cat", Digestion, 1975;12:17-24.

Jokinen, "Longitudinal Changes and Prognostic Significance of Cardiovascular Autonomic Regulation Assessed by Heart Rate Variability and Analysis of Non-Linear Heart Rate Dynamics", Academic Dissertation, Dept. of Internal Medicine, University of Oulu, 2003.

MacArthur et al., "Heart Rate Variability", Research Network on Socioeconomic Status and Health, 1997; http://www.macses.ucsf.edu/ResearchlAllostatic/notebook/heart.rate.html.

Hahn et al., "Stimulatory Effects on the Central Amygdaloid Nucleus on Pancreatic Exocrine Secretion in Rats", Neurosci. Letter Mar. 14, 1994; 169(1-2):43-46.

Richins, "The Innervation of the Pancreas", Journal Comp. Neurol. 1945; 82:223-236.

Durand, "Electric Stimulation of Excitable Tissue", The Biomedical Engineering Handbook, Chapter 17, 1995; 229-251.

Davison et al., "Plasma Osmolality and Urinary Concentration and Dilution During and after Pregnancy: Evidence that Lateral Recumbency Inhibits Maximal Urinary Concentrating Ability", British Journal of Obstetrics and Gynecology, 1981; 88(5):472-479.

Netter, "A Compilation of Paintings on the Normal and Pathologic Anatomy of the Digestive System, Part III Liver, Biliary Tract and Pancreas", The CIBA Collection of Medical Illustrations, 1957;1-31.

\* cited by examiner

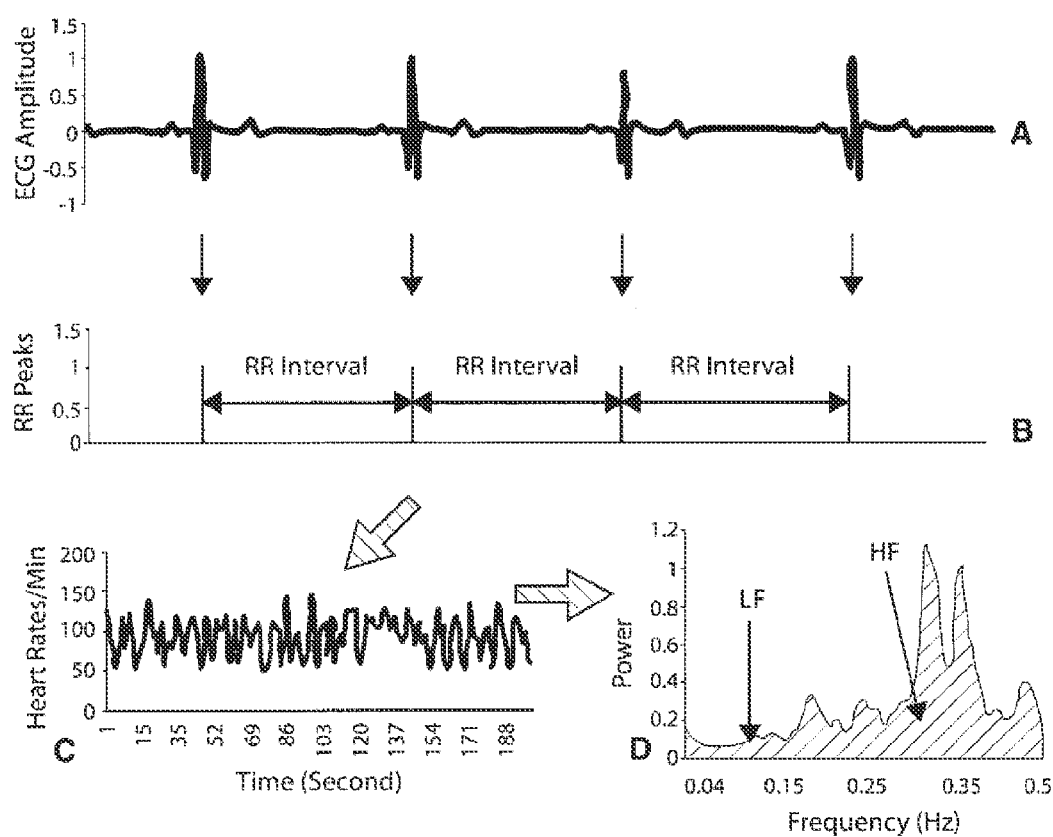

TREATMENT OF THE AUTONOMIC NERVOUS SYSTEM

RELATED APPLICATION

This application is based on, and claims benefit of, U.S. Provisional Application Ser. No. 60/585,885, filed on Jul. 7, 2004, which is hereby fully incorporated by reference.

FIELD OF THE INVENTION

The present invention relates to systems and methods for providing modulation of the autonomic nervous system by the electrical stimulation of the neuro-muscular system of a patient, and more particularly to an implantable electrical system for gastrointestinal stimulation, incorporating a heart rate sensor to indicate the neurovegetative patient condition, to initiate and terminate stimulation at specific locations, and an algorithm to automatically control electrical stimulation frequency, interval, amplitude, or a combination of such parameters for adaptive treatment of obesity, anorexia, other eating disorders, diseases related with the so called "metabolic syndrome" (e.g., impaired glucose tolerance and diabetes type 2, GERD, systemic hypertension, early arterovascular degeneration, early senility, and the like), and disorders related to a pathologic inbalance of the autonomic nervous system. The invention also includes provisions to minimize physician intervention, minimize requisite physician training, and facilitate patient follow-up in the treatment of such conditions.

BACKGROUND OF THE INVENTION

The autonomic nervous system (ANS) is the portion of the nervous system that controls the body's visceral functions, including action of the heart, movement of the gastrointestinal tract, and secretion by different glands, among many other vital activities, in order to maintain homeostasis of the body. Heart rate variability (HRV) measurement, also called heart period variability measurement, is a non-invasive tool for measuring the status of autonomic nervous system. Heart rate variability refers to the measurement of the regulation of the sinoatrial node, the natural pacemaker of the heart by the sympathetic and parasympathetic branches of the autonomic nervous system. The assumption when assessing HRV is that the beat-to-beat fluctuations in the rhythm of the heart provide an indirect measure of heart health, as a dynamic window into autonomic function and balance in sympathetic and vagus nerve activity. Simply put, HRV is the change in the length of time of consecutive heartbeats. As a matter of measurement convenience, a heartbeat is usually measured as the time (in msecs) from the peak of one R wave to the peak of the next. This time is referred to as the RR interval, the interbeat interval (IBI), or the heart period.

The changes in the length of normal RR intervals—that is, their variability—can be determined in different ways. Analysis is most commonly in either the time domain or the frequency domain. Time domain measurements use typical linear means of contrasting the individual RR intervals to the mean interval. An example of the many commonly applied time domain measurements is the standard deviation of the RR intervals. Frequency domain analysis uses non-linear methods such as Fast Fourier Transformation (FFT) or autoregressive analysis to determine at what frequencies the variability lies. This type of analysis has proven valuable because the physiological cause of the variability may be linked to certain frequency bands.

Recently chaos theory has also been applied to HRV analysis. Those arising from a normal sinus rhythm are considered. Ectopic beats and escape beats are not considered normal and are usually dealt with by systematically eliminating and smoothing of the remaining interval. HRV is characterized by four main components: the high frequency (HF) component (0.15 Hz to 0.40 Hz) measures the influence of the vagus nerve in modulating the sinoatrial node. The low frequency (LF) component (0.04 Hz to 0.15 Hz) provides an index of sympathetic effects on the heart, particularly when measured in normalized units. The very low frequency (VLF) component (0.003 Hz to 0.04 HZ) reflects the influence of several factors on the heart, including, for example, chemoreceptors, thermoreceptors, the renin-angiothensin system, and other non-regular factors. Almost all of the variability from a short-term spectral analysis of HRV is captured in these three components. An ultra low frequency (ULF) component (5.003 Hz) can also be observed in the HRV spectrum of a long sample.

The autonomic nervous system is linked and receives information from centers located in the spinal cord, brain stem, hypothalamus, and cerebral cortex. Furthermore, parts of the body send impulses by visceral reflexes into the centers in a dynamic, ongoing, multi-way dialogue, with each organ continuously influencing the others function. This communication network is based along two major ways: neurological (through the transmission of nerve impulses) and biochemical (via hormones and neurotransmitters).

The two major subdivisions of the transmission system of the ANS (i.e., the sympathetic and parasympathetic) regulate the body in response to an ever-changing internal and external environment. The sympathetic system is known as the "body accelerator." It activates the body and mind for exercise and work and it prepares the body to meet real or imagined threats to its survival. The parasympathetic system can be compared to a "brake." When the parasympathetic system is activated, we generally tend to relax and slow down. But each system can have inhibitory effects in some organs and excitatory effects in others. For example, the generally exciting sympathetic system inhibits the digestive musculature and by exciting the microvascular arteriolar sphincters, reduces the digestive blood flow. Conversely, the enervating parasympathetic system is extraordinarily exciting for the digestive system, and increases the visceral blood circulation.

Pacing of the stomach and other portions of the gastrointestinal (GI) tract via electrical pulses has been experimented with for some time. Most of the experimentation has been oriented toward improving the gastric emptying usually by attempting to speed up the transit time of food moving through the GI tract (for failure to thrive, gastroparesis, or pseudo-obstruction) or of relieving the neurally mediated symptoms associated with gastroparesis.

U.S. Pat. No. 5,423,872 (Jun. 3, 1995) to Cigaina for "Process and Device for Treating Obesity and Syndromes Related to Motor Disorders of the Stomach of a Patient" describes an implantable gastric electrical stimulator at the antrum area of the stomach which generates sequential electrical pulses to stimulate the entire stomach, thereby artificially altering the natural gastric motility to prevent emptying or to slow down food transit through the stomach. U.S. Pat. No. 5,423,872, however, has the inherent disadvantage that it is a stimulation device solely, and does not incorporate sensed triggered stimulation other than that of manual cycling provided by magnetic application, which potentially wastes energy by applying stimulation when it is not therapeutically required.

U.S. Pat. No. 5,690,691 (Nov. 25, 1997) to Chen et al. for "Gastro-intestinal Pacemaker Having Phased Multi-Point Stimulation" describes a portable or implantable gastric pacemaker employing a number of electrodes along the greater curvature of the stomach for delivering phased electrical stimulation at different locations to accelerate or attenuate peristaltic movement in the GI tract. The Chen et al. patent additionally provides a sensor electrode or a stimulation electrode wherein the response of an organ to an electrical stimulation pulse is sensed for delivering stimulation to a plurality of electrodes to provide phased electrical stimulation. However, Chen et al. is specifically directed to phase stimulation which progresses through the plurality of electrodes located along the peristaltic flow path and specifically senses the response of the organ to the electrical stimulation, but does not provide sensing of heart rate.

U.S. Pat. No. 5,836,994 (Nov. 17, 1998) to Bourgeois for "Method and Apparatus for Electrical Stimulation of the Gastrointestinal Tract" describes an implantable gastric stimulator which incorporates direct sensing of the intrinsic gastric electrical activity by one or more sensors of predetermined frequency bandwidth for application or cessation of stimulation based on the amount of sensed activity. The Bourgeois sensor does not contain algorithms to determine gastric rate variability.

U.S. Pat. No. 5,861,014 (Jan. 19, 1999) to Familoni for "Method and Apparatus for Sensing a Stimulating Gastrointestinal Tract On-Demand" relates to an implantable gastric stimulator for sensing abnormal electrical activity of the gastrointestinal tract so as to provide electrical stimulation for a preset time period or for the duration of the abnormal electrical activity to treat gastric rhythm abnormalities. Familoni also addresses recording of abnormal activity for a preset time period, but does not address altering of a normal gastric activity to achieve a variable result such as treatment for obesity.

U.S. Pat. No. 6,600,953 to Flesler et al. for "Acute and Chronic Electrical Signal Therapy for Obesity," addresses applying a non-excitatory electrical field to the stomach such that it increases the level of contraction of muscle tissue of the body of the stomach and decreases a cross sectional area of a portion of the stomach for a substantially continuous period of greater than about 3 seconds. Flesler applies a non-excitatory electrical field denoted as an Excitable-tissue control (ETC) signal that modifies the response of one or more cells to electrical activation so as to delay or prevent emptying of the stomach by increasing the level of contraction of stomach muscle(s) and thus narrowing the cross-sectional area of the stomach. Flesler invokes various singular sensors to initiate or terminate the ETC signal and incorporates patient activation and programmable timed periods of activation to attempt to achieve an acceptable life for the implantable device. The sensors are not intended to measure either HRV or GRV.

U.S. Pat. No. 6,571,127 to Ben-Haim et al. for "Method of Increasing the Motility of a GI Tract," addresses application of an non-excitatory electrical field excitable-tissue control signal to increase the contractile force and/or motility of a GI tract. The non-excitatory electric field is applied to reinforce (strengthen) a forward propagating wave and/or to inhibit (reduce) the response to the activation signal of a returning wave. Again, Ben-Haim does not provide sensors to measure HRV or GRV.

U.S. Pat. No. 5,928,272 shows a device and method to treat epilepsy, where electrical stimulation therapy is triggered based upon heart rate. This patent shows a correlation between a sudden change in heart rate and the potential for an epileptic seizure. Noting this sudden change, therapy can be induced to a nerve for the acute situation of halting or minimizing a seizure. The present application, on the other hand, has been recognized to be a treatment for different disease states outside the area of epilepsy, and is based upon heart rate variability analysis that does not involve a quick sudden rate of change as would be seen just prior to the onset of a seizure.

More recently, U.S. patent application Ser. No. 10/627,908 (filed Jul. 25, 2003) provides methods whereby an electrical stimulation device is implanted on the small intestines or lower bowel. All of these patents and patent applications, as well as all patents, patent applications, and publication cited herein, are hereby incorporated by reference in their entireties.

Similarly, in U.S. Patent Publications 2003/0181958 and 2003/0181959, Dobak describes a nerve stimulator which stimulates nerves of the sympathetic nervous system of body. In comparison, the present invention is aimed toward regulating the parasympathetic system of the body triggered from HRV.

SUMMARY OF THE INVENTION

The present invention provides improved devices and methods for treatment of obesity, especially morbid obesity, other eating related syndromes (e.g., anorexia), and other diseases related to a pathological balance of the autonomic nervous system. The devices and methods of this invention utilize a sensing element to monitor the patient's heart rate variability and compute the parasympathetic (P1) to parasympathetic (P2) ratio (P1/P2). Based upon the computed ratio, the sensing element then communicates with, and activates as appropriate, at least one gastric electrical stimulation device (GESD) attached to or adjacent to the stomach and/or an intestinal electrical stimulation device (IESD) attached to or adjacent to the small intestine. More than one GESD and/or IESD can be used if desired. The sensing element may communicate directly with both the at least one GESD and the at least one IESD. The sensing element may also communicate directly with the at least one GESD, which in turn is in communication with the at least one IESD. Preferably, the at least one GESD is attached to or is adjacent to, the lesser curvature (i.e., towards the pylorus) and the at least one IESD attached to or is adjacent to the duodenum and/or jejunum.

The present invention provides a method for treatment of a functional disorder related to balance of the autonomic nervous system with functional prevalence of the sympathetic or the parasympathetic component in a patient, said method comprising: implanting a first electrical stimulation device comprising one or more first electrical stimulation leads and a first electrical connector for attachment to a first pulse generator such that the one or more first electrical stimulation leads are attached to, or adjacent to, the patient's stomach, whereby electrical stimulation can be provided to the stomach through the one or more first electrical stimulation leads; implanting a second electrical stimulation device comprising one or more second electrical stimulation leads and a second electrical connector for attachment to the first or potentially a second pulse generator such that the one or more second electrical stimulation leads are attached to, or adjacent to, the patient's small intestines, whereby electrical stimulation can be provided to the patient's small intestines through the one or more second electrical stimulation leads; placing a sensing element on or in the patient's body to periodically monitor the patient HRV and compute the P1/P2 ratio, and wherein the sensing element, activates one or a plurality of pulse generators(s) to supply programmable electrical stimulation to the patient's GI tract; wherein the sensing element resumes monitoring and computation of the HRV ratio and further adjusts the pacing to achieve a desired ratio.

These and other features of the devices and methods of the present invention will be apparent from a consideration of the entire specification.

BRIEF DESCRIPTION OF THE DRAWINGS

FIG. 1 illustrates a general method to measure HRV signals and sympatho-vagal activity; Panel A is an original ECG tracing; Panel B is the detected RR wave peaks; Panel C is the derived HRV signal; and Panel D is the sympatho-vagal spectral features.

DETAILED DESCRIPTION

As noted above, heart rate variability (HRV) analysis is a non-invasive tool for measuring the status of autonomic nervous system. Similar considerations could be made for the gastric rate variability, which refers to the regulation of the natural gastric slow waves activity by the sympathetic and parasympathetic branches of the autonomic nervous system. Instead of measuring the RR cardiac interval, the peak-to-peak slow waves time or gastric period is considered; their mathematical analysis can reinforce and complement data obtained by HRV. By studying the variability of the heart and the gastric rate as well, we have a way to explore the ANS balance. The variable electrical activity of those organs is a placebo-free window for the body autonomic tuning.

Many diseases and pathologic conditions (e.g., diabetes, cardiac failure, obesity, stress, anxiety, hypertension, and the like) are associated with, and perhaps related to, a high basal sympathetic tone while a parasympathetic hyper-tone is benignly related with normal or hypo arterial tension, bradycardia, calmness, and usually long life expectancy.

The clinical experience accumulated so far upon a defined patient population with eating disorders, disclosed an evident correlation of anorexia and obesity with change in the normal balance of the HRV and GRV recording. In an obesity study, one of the present inventors studied 40 patients where the major component of the HRV was the very low frequency band (i.e., hyper tone of the sympathetic pathway). Almost all of the ten anorectic patients studied showed dominant the high frequency (HF) component (0.15 Hz-0.40 Hz; see FIG. 1D), which represents the parasympathetic pathway. Effectively, it is quite reasonable that anorexia is not a disease per se, since all metabolic and biochemical data of those patients are usually very good, and their only problem is the starvation. Their body system is regulated in an ideal manner. On the other hand, the obesity is part of a multifactorial syndrome, where diabetes type II, hypertension, short life expectancy, and similar conditions or factors are just a cohort of the alimentary disorder, which is not pathologic per se. The obese individual is genetically mildly or heavily set up as to live in a non stop alert condition, with the sympathetic system hyper-tuned; for that reason they introduce more calories and their satiety is set up for that. Until the digestive apparatus is well fitted for absorbing the excess food introduced, the obese patient will increase in weight, when the excess calories introduced overwhelm that function the patient will start a malabsorbitive condition which limits a further weight increase and the real disease starts (diarrhea, disprotidemia, vitamins deficiencies, liver disease, worsening hypertension, and the like).

By pacing the lesser curve of the gastric wall, but not exclusively, it is possible to tune up the balance between the low and high frequency to a safer ratio. Specific and personalized electrical parameters can move, in obesity for example, from a very low HRV to a higher and most healthy one. Unfortunately standard electrical parameters don't work in the same way, especially over the long term and continuous adjustments are often required.

The rich enervation of the gastric wall, and other parts of the digestive system, explains its role to be one of the most important neurological station of the body. A portion of all the digestive neurons is located in the gastric wall, and the most concentration of Dogiel type II cells (intramural plexuses) has been found there. The electrical stimulation of the gastric intramural nervous system has the direct consequence to move up or down the ANS balance, depending on what kind of electrical combined parameters are used.

The innovation of the present invention is of providing a continuous adjustment of the ANS balance by the pacing of the gastric wall with different electrical parameters based on HRV and GRV, in order to obtain the most useful ANS balance for a specific disease or pathological neurovegetative condition.

By normalizing the systemic hyper-tone of the sympathetic system the patient moves from an alert status to a normal one: blood pressure decreases, heart frequency decreases, the HRV becomes more "elastic," and the food intake is reduced. Generally all these effects are known as muscarinic activity. By turning from a hyper-sympathetic state to a normal one, an obese human being physiologically "brakes his body acceleration," reduces his food requests, and become normal, independently from the weight associated to that moment.

Furthermore, the production of mucous from the gastric wall increases and the acid drops, thereby providing reduced risk of peptic diseases. The tone of the lower esophageal sphincter increases. The two conditions ameliorate the gastroesophageal reflux disease and relieve specific symptoms. The intestinal motility increases and, as a consequence, the constipation is not a problem for those patients obtaining weight loss by gastric pacing. The systemic blood pressure reduces more than what expected by the simple weight loss because (a muscarinic consequence obtained by gastric pacing is the increased vascularization of the splancnic compartment) the systemic blood volume is shifted into the (vasodilated) splancnic district. Both the systolic and diastolic blood pressure reduce, as well the cardiac frequency. Also the glucose tolerance and insulin resistance improve because the parasympathetic tone is increased or the sympathetic is normalized.

Nevertheless, it is well recognized that physiological ageing is associated with a reduction in parasympathetic activity, and that in the healthy centenarians the HRV shows a higher value for the high-frequency component.

To increase the parasympathetic tone by gastric pacing it is useful also to accelerate or ameliorate the positive influence of the long-term endurance training on heart function. The submaximal exercise heart rate can be usefully controlled by the "demand stimulation" of the gastric myenteric plexuses and improve endurance sport performances.

An additional benefit of measuring heart rate and heart rate variability is saving battery life of the implantable pulse generator. In fact, during certain unpredictable conditions, the HRV assessing can show that, a very long off-time of gastric pacing or even no pacing at all can be positive in order to obtain the safer increased parasympathetic tone condition.

In studies concerning electrical stimulation of the gastrointestinal tract for morbid obesity, it has been discovered that selectively pacing the stomach by personalized electrical parameters, results in heart rate variability (HRV) changes in the sympathetic (P1) to parasympathetic (P2) ratio. Upon investigation, this interpretation of the data indicated a novel correlation between the HRV ratio and the weight of his patients. The HRV ratio for anorexics was in the 0.5 range or below 1, while the HRV ratio for the obese patient was in excess of 1.8 or over 1. It was also found that in pathologic conditions related to hyper-tone or to an exaggerated hypo-tone (for example the obese patient has a strongly chronic sympathetic tone with very low HRV while the anorectic with a very high HRV) and that the gastric pacing can be adjusted to provide a more or less parasympathetic HRV, depending on the clinical case.

Thus there is an opportunity for a novel stimulation device which can monitor HRV and deliver stimulation to adjust the P1/P2 ratio. The present invention provides such devices and methods.

Measurement and Analysis of Heart Rate Variability

Regular electrocardiogram (ECG) (FIG. 1A) can be recorded using abdominal surface electrodes. R-R intervals (FIG. 1B) can be derived from the ECG using a method of fuzzy neural network. A signal, called heart rate variability (HRV), can be derived after interpolation and sampling. An example of the HRV signal is presented in FIG. 1C. Smoothed power spectral analysis can then be performed on the HRV signal. Two parameters can be computed from the power spectrum; these parameters are LF (area under the curve in the low frequency band (0.04-0.15 Hz)) and HF (area under the curve in the high frequency band (0.15-0.50 Hz)) and are shown in FIG. 1D. It is well established that the LF reflects mainly sympathetic activity and partial vagal activity, where the HF represents purely vagal activity. In addition, the ratio, LF/HF, represents sympatho-vagal balance. The parameters HF and LF/HF can be used to assess vagal activity and the balance between sympathetic activity and vagal activity and then to coordinate and/or modify the electrostimulation parameters.

Detailed Description

Devices and methods for treatment of obesity (especially morbid obesity), other eating disorders (such as anorexia) syndromes, and diseases related to a pathological balance of the autonomic nervous system are provided. The devices and methods of this invention utilize a sensing element to monitor and compute the patients HRV ratio (P1/P2). The sensing element communicates with, and can activate, a gastric electrical stimulation device (GESD) attached to or adjacent to the stomach and/or an intestinal electrical stimulation device (IESD) attached to or adjacent to the small intestine. More than one GESD and/or IESD can be used if desired. The sensing element may communicate directly with the GESD and the IESD or with the GESD, which in turn is in communication with the IESD. Preferably, the GESD is attached to or is adjacent to, the lesser curvature (i.e., towards the pylorus of the stomach) or the fundus, and the IESD is attached to or is adjacent to the duodenum and/or jejunum.

As used herein, "communication" means the transmission and/or exchange of information, messages, or signals by any form. Examples include, but not limited to, communication through wired and wireless connections (e.g., electrical stimulation leads, digital signals, telemetric devices, transtelephonic programming, other radio frequency-based approach, and the like), whereby the communication proceeds from the sensing element to the electrical stimulation devices, pulse generations, and/or microprocessors In one embodiment, communication can proceed from the sensing element to both the gastric pulse generator and the intestinal pulse generator, whereby the gastric pulse generator supplies electrical stimulation to the patient's stomach and whereby the intestinal pulse generator supplies electrical stimulation to the patient's small intestine. Communication can also proceed from the sensing element to the gastric pulse generator and then to the intestinal pulse generator, whereby the gastric pulse generator supplies electrical stimulation to the patient's stomach and whereby the intestinal pulse generator supplies electrical stimulation to the patient's small intestine. Communication can also proceed from the sensing element to a single pulse generator, whereby the single pulse generator supplies electrical stimulation to both the patient's stomach and small intestine. Communication can also proceed from the sensing element to a microprocessor whereby the microprocessor communicates with the gastric pulse generator, the intestinal pulse generator and/or a single pulse generator by one of the means described herein As used herein, "sensing element" means one or more devices that receive, send, transmit, and/or respond to cardiac signals, specifically heart rate variability ratio. Such sensing element may include, but is not limited, to direct cardiac sensing leads and IEG monitoring electronics with storage and computational capability, external cardiac sensing leads and ECG monitoring electronics with storage and computational capability, internal sensing leads and implanted cardiac monitoring electronics with storage and computational capability. The sensing element may also include additional sensors to monitor patient's condition, activation from outside the body, activation by a telemetry device, activation by magnet, and/or activation by digital or radio frequency means. The additional sensors are utilized to qualify an HRV run to assess whether or not the patient was in a static cardiac condition (not undergoing an HRV response to exercise, emotion, illness, and/or the like).

The sensing is placed "on, or in the patient's body"; such placement is intended to cover various locations that are typically used to monitor cardiac activity. For example, the sensing element may be placed on the external surface of the chest or adjacent to the heart, within or external to the body, or within the cardiovascular system, and the like. The sensing element should detect, either directly or indirectly, cardiac heart rate activity (R-R interval). Thus, for example, the sensing element may be located on the outside of the chest and be activated at programmable time frames or sensor input to begin the HRV monitoring process. The sensing element would record/store/analyze about 3 to about 10 minutes of heart rate data (ECG strip). The strip would be qualified (by sensor input and mathematical calculation) to ensure that it represents resting cardiac activity. The sensing element would then analyze the rate variation of the strip for the parasympathetic and sympathetic components. The sensing element would then compute the HRV ratio, and dependent upon the value, communicate with the implanted pulse generator(s) to effect electrical stimulation Alternatively, the sensing element may be located within the body cavity and be activated a programmable timer, external communication, or qualifying sensor input. The implanted sensor could even be the metal housing of the implantable pulse generator. Alternatively, the sensing element may be located outside the body and be activated by the patient by any of the means described herein. Alternatively, the sensing element may include a plurality of sensors in a neural network and may be activated by any means described herein As noted, the devices and processes according to the invention include a sensing element that determines the resting/intrinsic HRV ratio and communicates with and/or activates the GESD and/or the IESD. After the sensing element communicates with and/or activates the electrical stimulation device or devices, the electrical stimulation device or devices artificially alters and preferably by means of sequential electrical pulses, the natural or original HRV ratio of a patient by electrical stimulation. More preferably, such sequential electrical pulses are generated by an electrical stimulator which is applied by laparoscopic means to a portion of, or adjacent to, the stomach or small intestines. Preferred locations for GESD include along the lesser curvature of the stomach. Preferred locations for IESD include along the duodenum and the jejunum. Of course, other portions of the stomach or small intestines can be electrically stimulated using the method of this invention. The sensing element may be placed on or within the body. The sensing element can be used to trigger the GESD and/or IESD at automatic predetermined, manually determined, or physiological sensor determined periods.

What is claimed is:

1. An implantable non-cardiac neuromuscular electro stimulator comprising:
    a pulse generator to provide electrostimulation;
    one or more leads with electrodes;
    a sensor to sense heart rate parameters; and
    a controller which, based upon sensed heart rate variability where the heart rate variability is based upon the sensed heart rate parameters, stimulates or withholds electrostimulation form the pulse generator through the one or more leads, wherein the controller performs embedded algorithms for the purpose of analyzing the heart rate variability, wherein the algorithms utilize frequency domain analysis, and wherein the frequency domain analysis utilizes auto regression type analysis.

2. The implantable non-cardiac neuromuscular electrostimulator of claim 1, further comprising a metal housing wherein the metal housing functions as the sensor.

3. The implantable non-cardiac neuromuscular electrostimulator of claim 1, wherein the algorithms also utilize time domain analysis.

4. The implantable non-cardiac neuromuscular electrostimulator of claim 1, wherein the frequency domain analysis also utilizes fast Fourier transformation methods.

5. An implantable gastro-intestinal neuromuscular pulse generator system comprising:
    a pulse generator to provide electrostimulation;
    one or more leads with electrodes for attachment to gastro-intestinal tissue; and
    a controller which stimulates or withholds electrostimulation, based upon sensed heart rate variability where the heart rate variability is based upon sensed heart rate parameters, to the gastro-intestinal tissue through the one or more leads.

6. The implantable gastro-intestinal neuromuscular pulse generator system of claim 5, wherein the sensed heart rate parameters include: length between heart heat intervals (R to R); length between intra-beat intervals (P-Q), (P-R), (R-T), (T-P), or any other combining lengths; length of T wave; or combinations thereof.

7. The implantable gastro-intestinal neuromuscular pulse generator system of claim 6, wherein the sensed heart rate parameters is the length between heart beat intervals (R to R).

8. The implantable gastro-intestinal neuromuscular pulse generator system of claim 6, wherein the sensed heart rate parameters are measured and compared prior to, and after, stimulation or withholding of electrostimulation.

9. A method of treating disorders of the body by gastro intestinal electrical stimulation comprising regulating the autonomic nervous system of a patient wherein regulating comprises sensing heart rate variability (HRV), computing an HRV ratio, and stimulating or withholding electrical stimulation based upon the ratio.

10. The method of claim 9, wherein an implantable non-cardiac neuromuscular electrostimulator is used to provide the gastro-intestinal electrical stimulation and wherein the implantable non-cardiac neuromuscular electrostimulator comprises a pulse generator to provide the electrostimulation; one or more leads with electrodes: and a controller whereby the electrostimulation may be provided to the patient through the one or more leads.

11. The method of claim 9, wherein the regulation of the autonomic nervous system includes a defined balance between parasympathetic and sympathetic nervous systems.

12. A method of treating a disorder of the autoimmune system comprising regulating the autonomic nervous system of a patient wherein regulating comprises sensing gastric or intestinal rate variability and, based upon the sensed gastric or intestinal rate variability, providing or withholding gastro-intestinal electrical stimulation.

13. The method of claim 12, further comprising sensing heart rate variability of the patient;
    wherein an implantable non-cardiac neuromuscular electrostimulator is used to provide the gastro-intestinal electrical stimulation;
    wherein the implantable non-cardiac neuromuscular electrostimulator comprises a pulse generator to provide electrostimulation: one or more leads with electrodes; and a controller, which, based upon the sensed heart rate variability and gastric rate variability, stimulates or withholds electrostimulation from the pulse generator through the one or more leads.

14. The method of claim 12, wherein the regulation of the autonomic nervous system includes a defined balance between parasympathetic and sympathetic nervous systems.

15. The method of claim 12, wherein providing or withholding gastro-intestinal electrical stimulation comprises providing or withholding electrical stimulation to gastro-intestinal tract tissue.

16. The method of claim 12, where providing or withholding gastro-intestinal electrical stimulation comprises providing or withholding electrical stimulation to a vagus nerve system or splanchnic nerve system.

17. A method of treating obesity by gastro intestinal electrical stimulation based upon the relationship between sensed heart rate variability and sensed gastric variability.

18. A method of electrically stimulating the gastro-intestinal tract during a body's sleep mode based upon sensed variability of heart rate or gastric rate.

19. A method for treatment of a functional disorder related to a the balance of the autonomic nervous system with functional prevalence of the sympathetic or the parasympathetic component in a patient, said method comprising:
    implanting a first electrical stimulation device comprising one or more first electrical stimulation leads and a first electrical connector for attachment to a first pulse generator such that the one or more first electrical stimulation leads are attached to, or adjacent to, the patient's stomach, whereby electrical stimulation can be provided to the stomach through the one or more first electrical stimulation leads;
    implanting a second electrical stimulation device comprising one or more second electrical stimulation leads and a second electrical connector for attachment to the first or potentially a second pulse generator such that the one or more second electrical stimulation leads are attached to, or adjacent to, the patient's small intestines, whereby electrical stimulation can be provided to the patient's small intestines through the one or more second electrical stimulation leads; and placing a sensing element on or in the patient's body to monitor the patient heart rate variability (HRV) and compute the P1/P2 ratio, and wherein the sensing element activates at least one of the first or second electrical stimulation devices to supply programmable electrical stimulation of the patient's GI tract;

wherein the sensing element resumes monitoring and computation of the HRV ratio and further adjusts the stimulation to achieve a desired ratio.

20. A method for treatment of a functional disorder related to a balance of the autonomic nervous system with functional prevalence of the sympathetic or the parasympathetic component in a patient, said method comprising:

implanting an electrical stimulation device comprising one or more electrical stimulation leads and an electrical connector for attachment to a pulse generator such that the one or more first electrical stimulation leads are attached to, or adjacent to, the patient's stomach, whereby electrical stimulation can be provided to the stomach through the one or more electrical stimulation leads; and placing a sensing element on or in the patient's body to monitor the patient heart rate variability (HRV) and compute an HRV ratio, and wherein the sensing element activates the electrical stimulation device to supply programmable electrical stimulation of the patient's stomach;

wherein the sensing element resumes monitoring and computation of the HRV ratio and further adjusts the stimulation to achieve a desired ratio.

* * * * *

UNITED STATES PATENT AND TRADEMARK OFFICE
CERTIFICATE OF CORRECTION

PATENT NO.       : 8,792,986 B2  
APPLICATION NO.  : 12/706608  
DATED            : July 29, 2014  
INVENTOR(S)      : Valerio Cigaina Page 1 of 1

It is certified that error appears in the above-identified patent and that said Letters Patent is hereby corrected as shown below:

On the title page of the patent, where the Assignee is listed:

"(73)   Assignee:    Medtronic, Inc., Minneapolis, MN (US)" should read  
-- "(73)   Assignee:    Medtronic Transneuronix, Inc., Minneapolis, MN (US)" --

Signed and Sealed this  
Tenth Day of November, 2015

Michelle K. Lee  
*Director of the United States Patent and Trademark Office*

UNITED STATES PATENT AND TRADEMARK OFFICE
CERTIFICATE OF CORRECTION

PATENT NO.        : 8,792,986 B2
APPLICATION NO.   : 12/706608
DATED             : July 29, 2014
INVENTOR(S)       : Valerio Cigaina It is certified that error appears in the above-identified patent and that said Letters Patent is hereby corrected as shown below:

TITLE PAGE:

This certificate supersedes the Certificate of Correction issued November 10, 2015.
Item [73], Assignee,
"Medtronic Transneuronix, Inc., Minneapolis, MN (US)"

(as corrected to read in the Certificate of Correction issued November 10, 2015) is deleted and patent is returned to its original state with the assignee name in patent to read -- Medtronic, Inc., Minneapolis, MN (US) --

This certificate supersedes the Certificate of Correction issued November 10, 2015.

Signed and Sealed this
Twenty-second Day of December, 2015

Michelle K. Lee
*Director of the United States Patent and Trademark Office*